Aug. 20, 1935. J. H. NICOLAS Plant Pat. 137
ROSE
Filed March 28, 1935
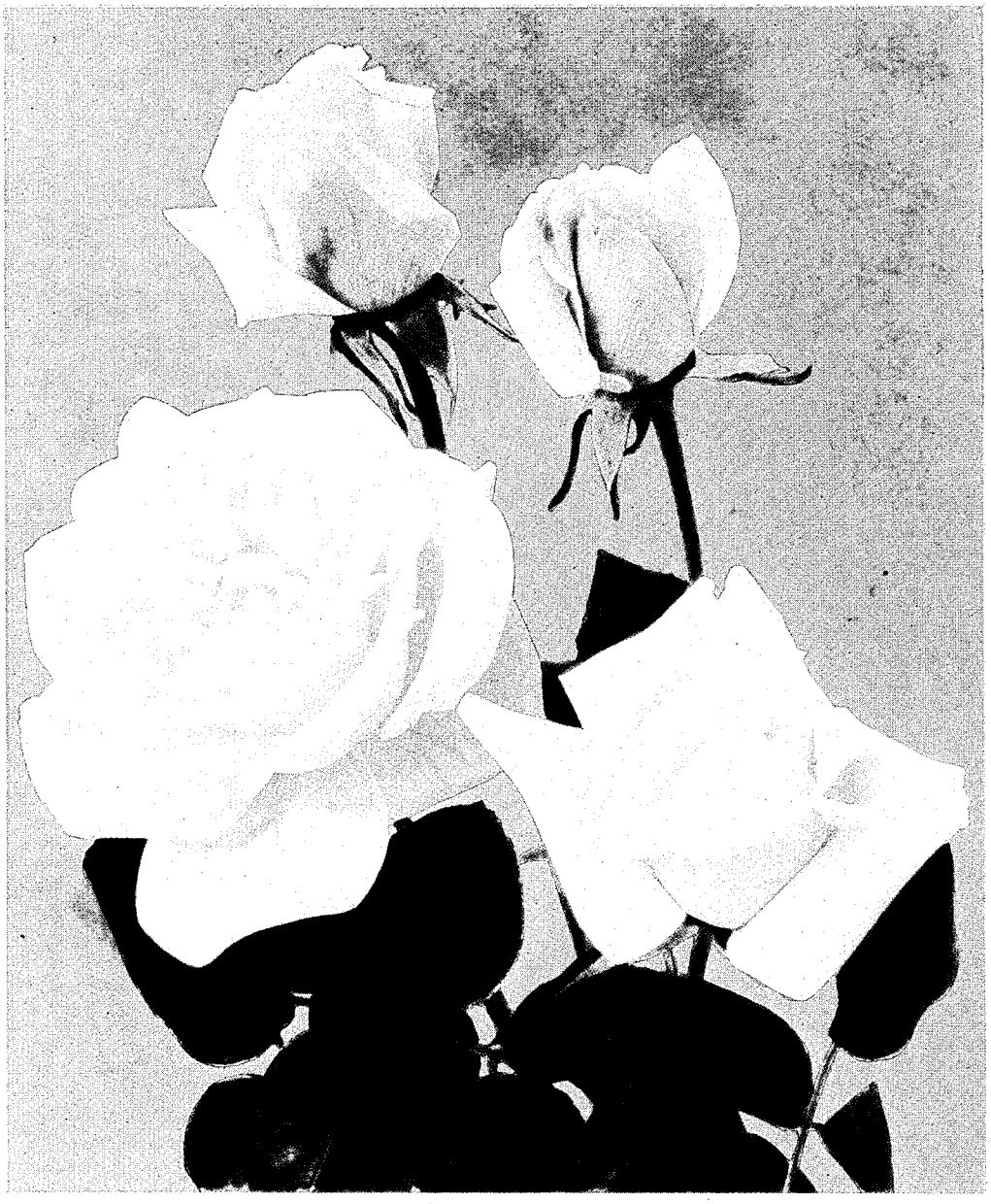
Inventor
J. H. Nicolas
By Robert Robb
Attorney Patented Aug. 20, 1935

UNITED STATES PATENT OFFICE

137

ROSE

Jean H. Nicolas, Newark, N. Y., assignor to
Jackson & Perkins Company, Newark, N. Y.

Application March 28, 1935, Serial No. 13,559

1 Claim. (Cl. 47—61)

The present invention relates to a new and distinct variety of rose plant, characterized both by the novelty of its color and its growing habit, by virtue of which it is adaptable for florist as well as garden use.

Asexual reproduction has proved that this new variety, as a forcing rose, is unique in color and fills a gap heretofore existing in the color range of commercial cut flowers. Another feature of the rose of great value to flower growers is its habit of growing without that form of pruning known as pinching, stems of a length and strength generally obtainable in other varieties only by the pinching process. This feature greatly reduces cost of production of long stemmed fancy roses. The rose is full and of classical form,—fully double.

From the standpoint of qualifications for garden usage (that is, for use as a garden rose), the plant is robust and very floriferous, giving also stems of a length unusual in outdoor growing.

The present variety is similar in some respects to the known variety "Los Angeles", but is a better grower and a great improvement thereover in many other respects.

The variety has been extensively reproduced asexually and the characteristics herein given have been found to be fixed.

The following is a detailed description of my new variety:

Parentage:
Seedling.
*Seed parent.*—"Chas. P. Kilham."
*Pollen parent.*—"Mrs. Pierre S. du Pont".

Classification:
*Botanic.*—Hybrid tea.
*Commercial.*—Hybrid tea.

*Flower*

Blooming habit:
Intermittent.

Bud:
*Size.*—Very large.
*Form.*—Long, ovoid; unaffected by wet or hot weather.
*Color.*—(Gravereaux color system): When sepals first divide—pink with tawny suffusion. When petals begin to unfurl—pink suffused yellow. When half blown; inside of petals salmon pink, reverse of petals slightly paler.
*Sepals.*—Smooth edge; curl back when buds open.
*Calyx.* — Shape — funnel. Size—large. Aspect—smooth. Odor when rubbed—none.
*Peduncle.* — Length — very long. Aspect — smooth. Color — medium green. Strength —stiff, heavy.
*Opening.*—Bud opens well; unaffected by adverse conditions.

Bloom:
*Size.*—Very large. Average size when fully expanded 4".
*Borne.*—Singly.
*Stems.*—Very long and heavy; strong.
*Form.*—When first open globular. Permanence—flattens; outer petals curl back.
*Petalage.*—Double (full but open center). Number of petals under normal conditions 30 to 35.
*Color.*—Center of flower rosy salmon. Outer petals salmon pink. Base of petals (aiglet) yellow. Inside of petals rosy salmon. Reverse of petals pale pink suffused salmon. General tonality from a distance salmon pink.
*Variegations.*—None.
*Discoloration.*—General tonality at end of first day rosy salmon; second day salmon pink; third day salmon.

Petals:
*Texture.*—Thick; unaffected by wet or hot weather.
*Appearance.*—Inside satiny; outside satiny.
*Form.*—Round.
*Arrangement.*—Informal (with "rags" in center). Petaloids in center many, large.
*Persistence.*—Drop off cleanly.
*Fragrance.*—Moderate. Nature—tea (average hybrid tea scent).
*Lasting quality.*—On the plant very long and as a cut flower unusually long lasting.

Genital organs:
*Stamens, anthers.*—Large, few. Color—yellow. Arrangement—regular around styles, tucked in calyx partly.
*Stamens, filaments (threads).*—Long. Color—white.
*Pollen.*—Lemon yellow.
*Styles.*—Loosely separated; uneven length; medium length and heavy.
*Stigmas.*—Color white.
*Ovaries.*—Exclosed in calyx, some protruding from calyx.

Fruit:
Variety is sterile with its own pollen.

*Plant*

Form:
Bush.

Growth:

Very vigorous, branching.

Foliage:

*Leaflets.*—Generally 5, sometimes 7.

*Size.*—Very large.

*Quantity.*—Abundant.

*Color.*—New foliage—upper side bronzy; under side bronzy. Old foliage—upper side dark green; under side dark green.

*Shape.*—Oval pointed.

*Texture.*—Upper side leathery; under side smooth.

*Ribs and veins.*—Ordinary.

*Edge*—Serrated (saw toothed).

*Leaf stem.*—Color reddish; under side smooth.

*Stipules.*—Medium length, smooth.

*Disease resistance.*—Resistant.

Wood:

*New wood.*—Color reddish; bark smooth.

*Old wood.*—Color green, brown; bark smooth.

Thorns (divided into thorns, prickles and short needles):

*Thorns.*—Quantity—on main stalks from base few; on laterals from stalk few. Form—broad base, medium length, straight. Color when young red. Position irregular.

*Prickles.*—Quantity—on main stalks none; on laterals none.

*Short needles.*—Quantity—on main stalks none; on laterals none.

I claim:

A new and distinct variety of rose plant, characterized by its growing habit which makes it adaptable both for florist and garden usage, and the unique color of its bloom, substantially as described and shown.

JEAN H. NICOLAS.